(12) United States Patent
Utsunomiya et al.

(10) Patent No.: US 7,944,564 B2
(45) Date of Patent: May 17, 2011

(54) DEVICE AND METHOD FOR ACQUIRING INFORMATION ON OBJECTIVE SUBSTANCE TO BE DETECTED BY DETECTING A CHANGE OF WAVELENGTH CHARACTERISTICS ON THE OPTICAL TRANSMITTANCE

(75) Inventors: Norihiko Utsunomiya, Machida (JP); Mitsuro Sugita, Tokyo (JP); Satoru Nishiuma, Kawasaki (JP); Takao Yonehara, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/642,446

(22) Filed: Dec. 18, 2009

(65) Prior Publication Data

US 2010/0097612 A1 Apr. 22, 2010

Related U.S. Application Data

(62) Division of application No. 11/659,717, filed as application No. PCT/JP2005/017326 on Sep. 14, 2005, now Pat. No. 7,659,987.

(30) Foreign Application Priority Data

Sep. 16, 2004 (JP) .................................. 2004-270501
Sep. 16, 2004 (JP) .................................. 2004-270572
Sep. 16, 2004 (JP) .................................. 2004-270574

(51) Int. Cl.
*G01N 22/00* (2006.01)
(52) U.S. Cl. ....................................... 356/446; 356/445
(58) Field of Classification Search ........... 356/445–448
See application file for complete search history.

(56) References Cited

U.S. PATENT DOCUMENTS

| 6,183,696 | B1 | 2/2001 | Elkind et al. |
| 6,441,906 | B2* | 8/2002 | Dickopf et al. ................ 356/445 |
| 6,862,398 | B2* | 3/2005 | Elkind et al. .................. 356/445 |

(Continued)

FOREIGN PATENT DOCUMENTS

| EP | 0 797 090 A2 | 9/1997 |
| EP | 0 973 023 | 1/2000 |
| JP | 10-19768 A | 1/1998 |

(Continued)

OTHER PUBLICATIONS

Takayuki Okamoto, et al., "Local plasmon sensor with gold colloid monolayers deposited upon glass substrates", Optics Letters, vol. 25, No. 6, Mar. 15, 2000, pp. 372-374.

*Primary Examiner* — Michael P Stafira
(74) *Attorney, Agent, or Firm* — Fitzpatrick, Cella, Harper & Scinto

(57) ABSTRACT

An information-acquiring device for acquiring information on an objective substance to be detected, which is provided with a sensing element that has a surface capable of fixing the objective substance to be detected thereon, and makes applied light change its wavelength characteristics in response to the fixed state of the objective substance to be detected onto the surface, a light source, and light-receiving means for receiving light emitted from the light source through the sensing element, has the light-receiving means and the light source arranged on the same substrate so that the light which has been emitted from the light source and has been transmitted through the sensing element can be led to the light-receiving means, and has means for varying the wavelength regions of each light incident on each of a plurality of the light-receiving means installed in an optical path from the light source to the light-receiving means.

7 Claims, 13 Drawing Sheets

U.S. PATENT DOCUMENTS

| | | |
|---|---|---|
| 6,956,651 B2 | 10/2005 | Lackritz et al. |
| 7,057,731 B2 * | 6/2006 | Naya .............................. 356/445 |
| 7,384,561 B2 | 6/2008 | Utsunomiya |
| 7,387,901 B2 | 6/2008 | Nishiuma et al. |
| 7,399,445 B2 * | 7/2008 | Kuroda et al. ................... 422/55 |
| 2006/0170918 A1 | 8/2006 | Nishiuma |
| 2007/0105087 A1 | 5/2007 | Ban et al. |
| 2007/0248571 A1 | 10/2007 | Masada et al. |
| 2009/0053174 A1 | 2/2009 | Kaneko et al. |
| 2009/0060869 A1 | 3/2009 | Sugita et al. |

FOREIGN PATENT DOCUMENTS

| | | |
|---|---|---|
| JP | 10-221245 A | 8/1998 |
| JP | 2000-356587 | 12/2000 |
| JP | 2000-356587 A | 12/2000 |
| JP | 2002-148182 A | 5/2002 |
| JP | 2003-344280 A | 12/2003 |
| JP | 2004-245638 A | 9/2004 |
| WO | 00/46589 | 8/2000 |
| WO | 02/055993 | 7/2002 |

* cited by examiner

US 7,944,564 B2

DEVICE AND METHOD FOR ACQUIRING INFORMATION ON OBJECTIVE SUBSTANCE TO BE DETECTED BY DETECTING A CHANGE OF WAVELENGTH CHARACTERISTICS ON THE OPTICAL TRANSMITTANCE

This application is a divisional of application Ser. No. 11/659,717, which was the National Stage of International Application No. PCT/JP2005/017326, filed Sep. 14, 2005. The contents of each of the foregoing applications is incorporated herein by reference.

TECHNICAL FIELD

The present invention relates to a device for acquiring information on an objective substance to be detected by detecting a change of wavelength characteristics on an optical transmittance in a system containing the objective substance to be detected, and to a method for acquiring the information on the objective substance to be detected by using the device.

BACKGROUND ART

In recent years, with increasing awareness of health issues, environmental issues and security issues, techniques for detecting trace amounts of biological substances and chemical substances relating to these issues have been demanded. As the techniques for detecting these objective substances to be detected, many techniques are suggested which measure the change of optical properties of a liquid specimen caused by the interaction of the specimen including the substances to be detected with a reagent or a sensor element. As for the methods for optically detecting these substances to be detected, many techniques of detecting the change of spectrum are proposed and/or developed as followings:

(1) a technique for detecting the change of an absorption spectrum caused by a reaction product produced through a chemical reaction including an enzyme reaction, or detecting the change of an absorbance for a particular wavelength; and (2) a technique for detecting the change of the absorption spectrum or the absorbance for the particular wavelength by an agglomerate, through forming the agglomerate of fine particles through the substances to be detected, with the use of fine particles which immobilize a capturing body specifically coupled with the substances to be detected thereon.

These techniques acquire information by measuring spectrum with the use of a spectroscope, and accordingly have a problem of needing a period of time for scanning a necessary region of wavelengths.

The problem can be improved by using a polychromator and an arrayed type detecting element, which eliminating the need for scanning the wavelengths. However, the device has constraint in the disposition of a light source, a sensing part for introducing a specimen and treating it for measurement, the polychromator and a detecting element for detecting the optical properties, and leaves the problem unsolved that the device is hardly miniaturized.

In addition, there is a sensor by using a surface plasmon resonance technique as is described in U.S. Pat. No. 6,183,696, as an example of solving the above described miniaturization problem by adopting a detecting technique without depending on the change of an absorption spectrum. The invention according to U.S. Pat. No. 6,183,696 has a characteristic in solving a problem of a mechanism for detecting a resonance angle, which has been a problem of the conventional surface plasmon resonance technique, by diffusive incident light and adopting a photodiode array. An advantage of this sensor is a point of simplifying a configuration of a detecting device, because of having a light-emitting element and a light-receiving element formed on the same plane. However, the device needs a length corresponding to a resonance angle in a contacting part with a specimen, or equivalently, needs a large size of a sensor surface for detecting one objective substance to be detected, and accordingly has a constraint for simultaneously detecting a plurality of the substances to be detected.

As a technique of solving the problem of a sensor area for detecting the above described one objective substance to be detected, among techniques using plasmon resonance, Japanese Patent No. 3452837 describes a sensor with the use of a localized plasmon resonance of metallic nanoparticles. A sensor element with the use of the localized plasmon resonance has an advantage of needing a very small area for a detecting element because of using metallic nanoparticles. However, the sensor element needs to detect a transmission spectrum or a reflection spectrum, and accordingly still leaves the same problem as in the above described technique of detecting the spectrum.

In addition, EP 1157266A1 discloses a sensor provided with a sensor chip having sensor chip units integrated crosswise and a phototransducer having the arrays of the phototransducer integrated crosswise, as a compact surface plasmon resonance sensor. FIG. 4(a) shows a disclosed sensor having a light source and a detecting element array arranged on the same substrate, and a perception region of a sensor chip and a diffraction grating installed in an optical path between the light source and the detecting element array. The sensor disclosed here is persistently the surface plasmon sensor which reflects an emitted light from a light source by the sensor chip and introduces the reflected light to the detecting element array. In addition, the document does not describe a method of detecting a light which has been transmitted through the sensor chip and an application to the localized plasmon resonance.

DISCLOSURE OF THE INVENTION

The present invention is designed for miniaturizing both a sensing element portion and a detecting device, in a technique for detecting an objective substance to be detected with the use of spectrum characteristics for wavelengths. Furthermore, the present invention provides a device for acquiring information on the objective substance to be detected, which is suitable for using localized plasmon resonance.

According to an aspect of the present invention, there is provided an information-acquiring device for acquiring information as to an objective substance to be detected, comprising a sensing element which has a surface capable of fixing the objective substance to be detected thereon and makes an applied light change its wavelength characteristics in response to a fixed state of the objective substance to be detected onto the surface, a light source, and a plurality of light-receiving means for receiving light emitted from the light source through the sensing element, wherein the device has the light-receiving means and the light source arranged on the same substrate, the light emitted from the light source and transmitted through the sensing element is led to the light-receiving means, and a means for varying the wavelength regions of each light incident on each of a plurality of the light-receiving means is installed in an optical path from the light source to the light-receiving means.

The means for varying the wavelength region of each light incident on each of a plurality of the light-receiving means is preferably a spectral means.

The sensing element may be arranged in a light path between the spectral means and the light source.

Alternatively, the sensing element may be arranged in a light path between the spectral means and a plurality of the light-receiving means.

The information-acquiring device may have further a reflecting means for leading light from the light source to the light-receiving means through the sensing element. The reflecting means may be made of a concave mirror which focuses spectral light made by the spectral means on the light-receiving means.

The device may have a plurality of the light sources, enables each of a plurality of the light sources to selectively emit light by using a means for switching the light source and varies the wavelength of the light to be received by the light-receiving means by using the spectral means.

The means for varying the wavelength region of each light incident on each of a plurality of the light-receiving means may be an optical filter.

The device may acquire information on the objective substance to be detected by using plasmon resonance. The sensing element preferably has a surface which can fix a metallic nanoparticle capable of capturing the objective substance to be detected thereon, and the plasmon resonance is a localized plasmon occurring around the metallic nanoparticle fixed on the surface.

The light source and the light-receiving means may be formed on the same semiconductor substrate.

According to another aspect of the present invention, there is provided an information-acquiring method for acquiring information on an objective substance to be detected in a specimen by using a sensing element characterized in that the method comprises the steps of:

preparing the sensing element having the objective substance to be detected fixed thereon;

when light emitted from the light source illuminates the sensing element having the objective substance to be detected fixed thereon, and the transmitted light of emitted light is led to a plurality of the light-receiving means placed on the same substrate as the light source is placed, varying the wavelength of each light to be received by each of a plurality of light-receiving means, through a wavelength-varying means installed in an optical path from a light source to the light-receiving means, and acquiring the wavelength characteristics on the transmittance of every wavelength of the light which has passed through the sensing element and has been received by each light-receiving means; and determining the coupled amount of the objective substance to be detected which has been coupled with the sensing element, on the basis of the wavelength characteristics.

The wavelengths of light to be received may be varied by a spectral means. In the method, a plurality of the light sources may be prepared, and the wavelengths of the light to be received by the light-receiving means are varied according to the positions of a plurality of the light sources.

In the method for acquiring information on the objective substance to be detected, the wavelength of the light to be received may be varied by an optical filter.

The present invention provides a device which acquires information on an objective substance to be detected by using a transmitted light that has been transmitted through a sensing element, and which is suitable for a sensor that uses localized plasmon resonance. The device can be miniaturized because of arranging a light source and light-receiving means on the same substrate, and installing means for changing a wavelength region of a light incident on each of a plurality of light-receiving means in an optical path from the light source to the light-receiving means. Furthermore, the device does not need a mechanical drive in acquiring a wavelength spectrum, and accordingly can shorten a period of time necessary for acquiring the spectrum, or equivalently, an analysis period of time. In addition, the device arranges electric elements of the light source and the light-receiving means on a single substrate, and accordingly simplifies an electric interface and a device configuration. Furthermore, the device has improved workability when performing maintenance.

BRIEF DESCRIPTION OF THE DRAWINGS

In each drawing, the same reference characters are used for the same parts.

BEST MODE FOR CARRING OUT THE INVENTION

Summaries of an information-acquiring device and an information-acquiring method for acquiring information on an objective substance to be detected provided by the present invention will be now described referring to FIGS. 1, 2, 4 and 7.

A sensing element 104 has surface capable of fixing the objective substance to be detected thereon. The objective substance to the detected is introduced into the sensing element mainly in a form of a liquid specimen containing the substance, and is fixed to the surface of the sensing element. The substances to be detected are roughly classified into non-biological and biological substances. The non-biological substance among the objective substances to be detected, which increase an industrial utility value of the present invention, include PCB, dioxins and endocrine disrupting chemicals so-called environmental hormones. The biological substances include nucleic acid, protein, sugar chain, lipid and complexes thereof, such as deoxyribonucleic acid, ribonucleic acid, an aptamer, a gene, a chromosome, a cell membrane, a virus, an antigen, an antibody, a lectin, a hapten, a hormone, a receptor, an enzyme, a peptide, a sphingoglycolipid and a sphingolipid. Furthermore, bacteria and cells themselves can be the biological substances to be detected by the device according to the present invention.

A light source 102 emits a light for illuminating a sensing element, of which the wavelength characteristics change corresponding to a captured state of the objective substance to be detected. The emitted light is transmitted through the sensing element, and is led to a light-receiving means 103 installed on the same substrate as the light source.

Means for varying each wavelength region (hereafter called "wavelength-varying means") is installed in a light path between the light source and the light-receiving means. The wavelength-varying means varies each wavelength or wavelength region of the light incident on each of the light-receiving means 103. By varying the wavelength, the sensing element can determine the transmittance of the light in each wavelength or wavelength region. Specifically, the present invention provides a device which can know the presence or absence of absorption in the predetermined wavelength regions and an absorbed amount, by making the wavelength-varying means divide a wavelength region relating to a wavelength absorption spectrum, and making a plurality of the light-receiving means receive a plurality of the obtained wavelengths or wavelength regions.

Figure 1:
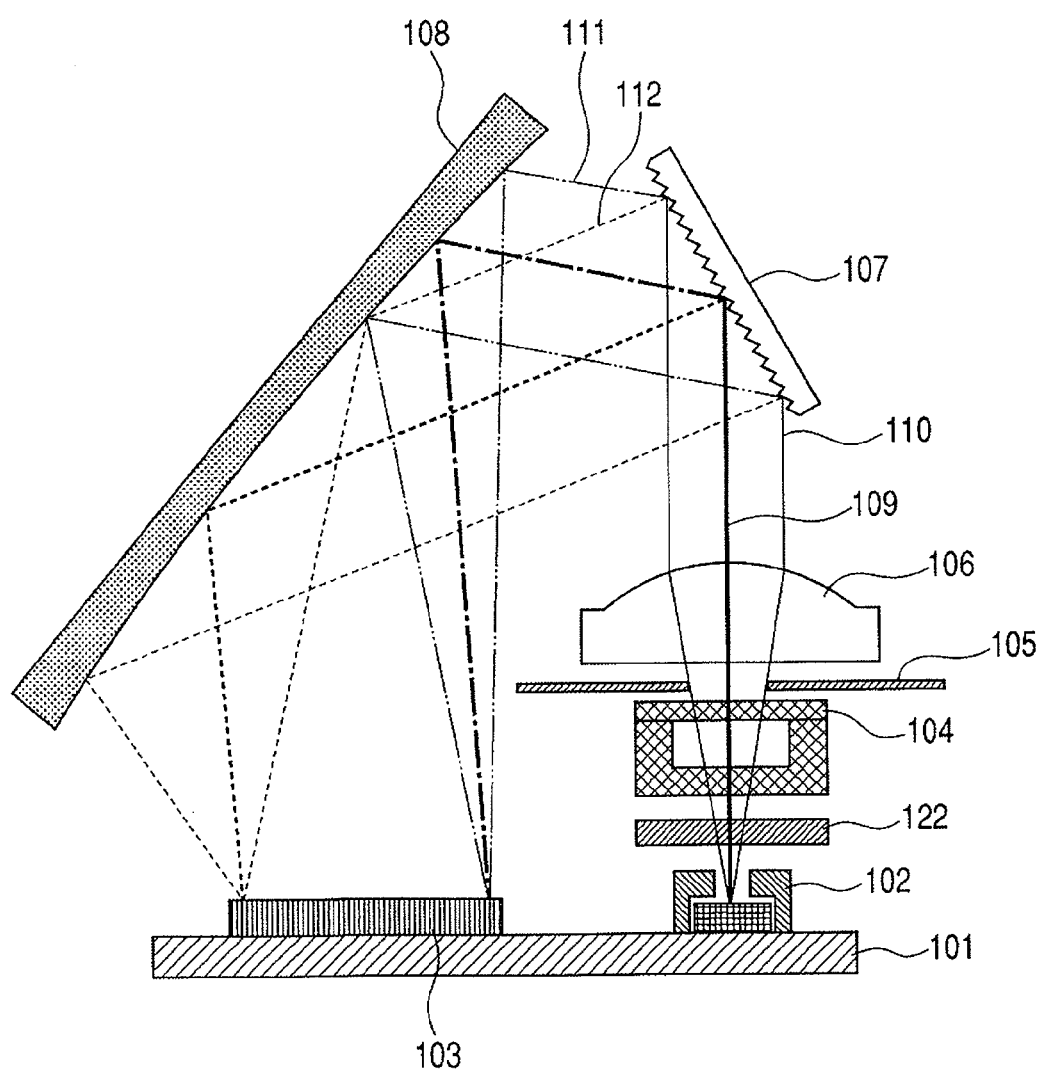
FIG. 1 is a schematic block diagram showing one example of an information-acquiring device.
Figure 2:
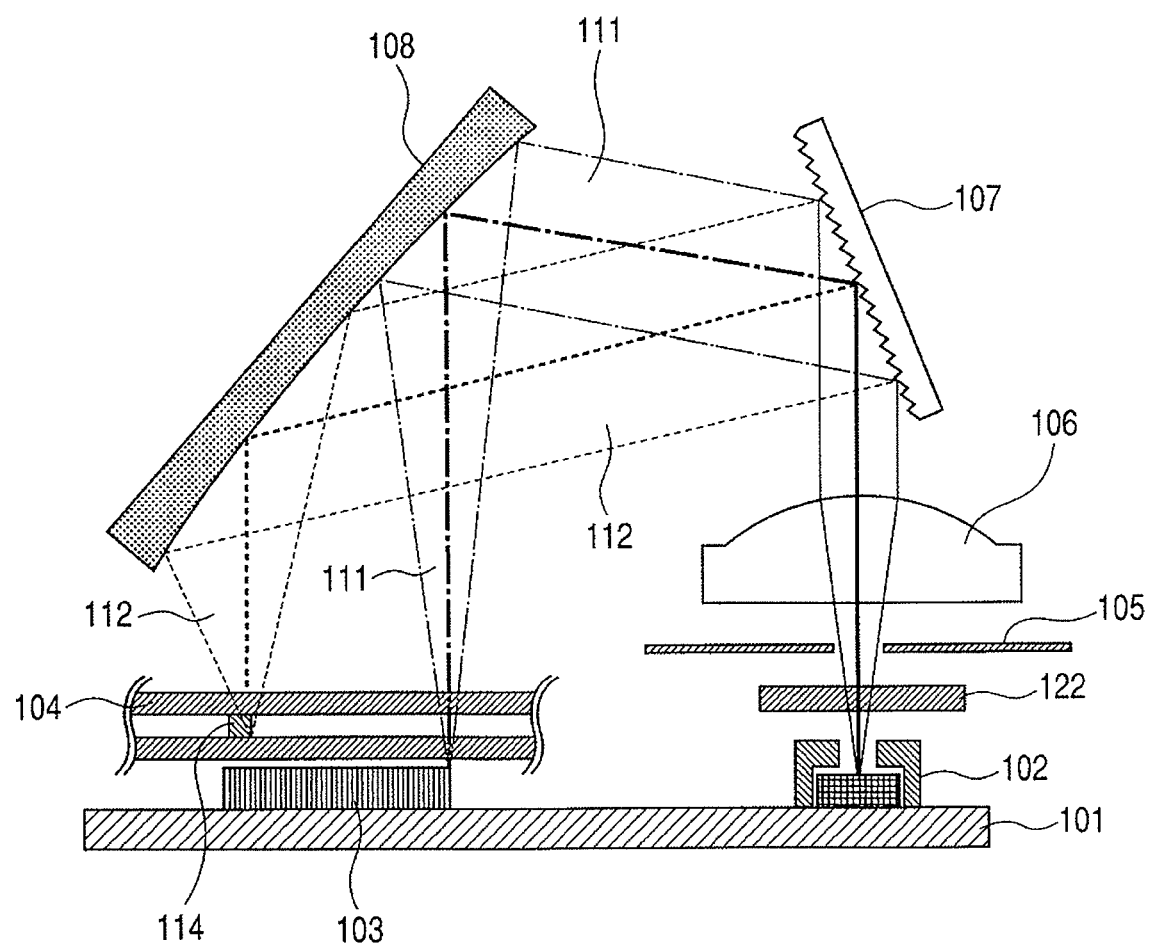
FIG. 2 is a schematic block diagram showing one example of an information-acquiring device.

In the present invention, there are two aspects of arranging the sensing element 104 in the light path from the light source 102 to spectral means 107 as shown in FIG. 1, and of arranging the sensing element 104 in the light path from spectral means 108 to the light-receiving means 103 as shown in FIG. 2.

Aspects according to the present invention will be now described under the sensing element and an optical configuration except it.

(Sensing Element)

It is known that when a metallic nanoparticle exists on the surface of a transparent substrate, an applied light onto the substrate is greatly absorbed in a particular wavelength due to localized plasmon resonance. The absorbed peak wavelength changes according to a refractive index around the metallic nanoparticle.

When a metallic nanoparticle changes the surface condition through capturing a substance to be detected onto its surface, the refractive index around the metallic nanoparticle is changed, and an absorbed peak wavelength of the applied light is shifted. By detecting the shifted amount, a sensing element can determine the presence or absence and the captured amount of the substance to be detected.

FIGS. 10A to 10D show an example of a sensing element with the use of a localized plasmon resonance technique using the metallic nanoparticle. The sensing element is composed of: a main body consisting of a substrate 401 having a groove 403 of a channel for passing a liquid specimen formed thereon and a lid 404 of the groove; and the metallic nanoparticle 402 fixed in the main body.

Figure 10A:
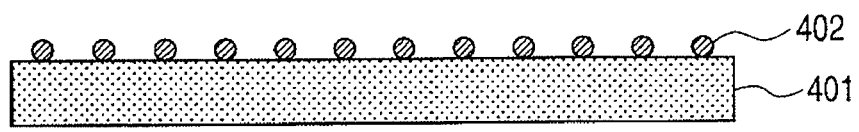
FIGS. 10A, 10B, 10C and 10D are views showing a sensing element using localized plasmon resonance.
Figure 10B:
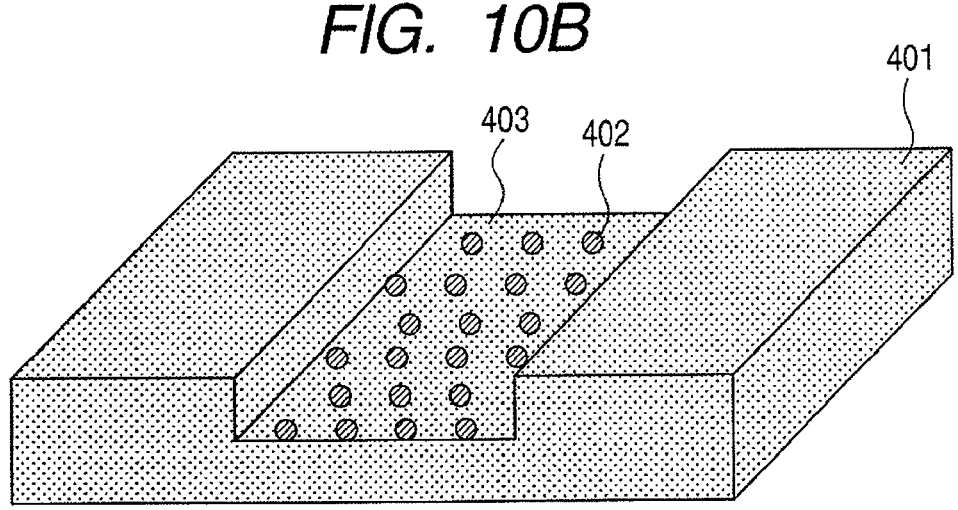
Figure 10C:
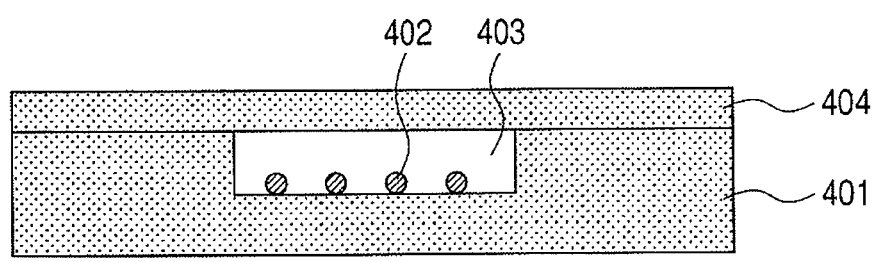

FIG. 10A is a side view showing the state of the metallic nanoparticle fixed in the main body of the sensing element. FIGS. 10B and 10C show the state of a metallic nanoparticle 402 fixed on the bottom face of a groove 403 of a substrate 401. However, an aspect of fixing the metal nanoparticle not on the groove surface but on the surface which composes the channel of a channel lid 404 is acceptable. The substrate 401 and the lid 404 are preferably made of an optically transparent material, but are not always required to be transparent and have to have the surface which reflects an enough light for measurement when used in a configuration of detecting a reflected light.

Figure 10D:
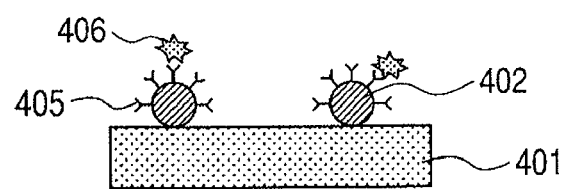

A metallic element constituting a metallic nanoparticle 402 may be any element as long as it can cause a localized plasmon resonance phenomenon, but is preferably gold or silver. FIG. 10D is an enlarged view showing the state of the metallic nanoparticle fixed in the main body of the sensing element. A capturing body 405 which forms a specific coupled pair with the objective substance to be detected, such as antigen/antibody, complementary DNA, receptor/ligand and enzyme/substrate, is immobilized on the metallic nanoparticle 402, and the substance 406 to be detected is captured by the capturing body 405.

Figure 11:
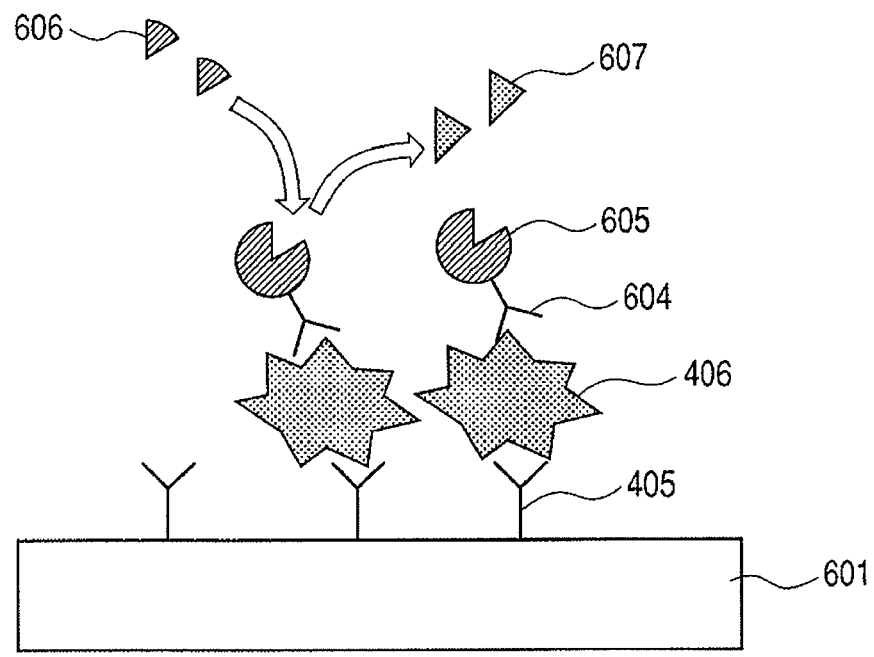
FIG. 11 is a view showing a sensing element using an enzyme label.

FIG. 11 shows one example of a detecting technique using an enzyme label. The capturing body 604 which specifically is coupled to the objective substance to be detected is prepared, and is labeled with an enzyme 605. On the other hand, the capturing body 405 is immobilized on a substrate 601 such as substrate 401 and lid 404 in FIG. 100 with a usual method. The sensing element makes the capturing body capture the objective substance to be detected, and then makes the objective substance coupled with the labeled capturing body 604. The sensing element reacts the enzyme 605 with an enzyme substrate 606 corresponding to the enzyme 605 to produce an enzyme reaction product 607.

The above described components which can be adopted in the example of a detecting technique will be described below. A substrate 601 comprises a material transparent sufficient for measuring a transmitting light in the case of measuring the transmitting light, and a material having a reflective face sufficient for measuring a reflective light in the case of measuring the reflective light. A capturing body 405 and 604 includes an antibody which is specifically coupled with the objective substance to be detected. An enzyme 605 includes horseradish peroxidase, alkaline phosphatase and β-galactosidase, but is not limited to only the enzyme as long as the enzyme can produce an enzyme reaction product 607 which has optical characteristics of having absorption in a particular wavelength, for instance, 491 nm. An enzyme substrate 606 to be used can be a substance which is usually used in combination with these enzymes. The substance is, for instance, 1,2-phenylenediamine. When the enzyme reaction product has an optical characteristic of having absorption in a particular wavelength, the absorption spectrum of a transmitted light has the characteristic originated in the enzyme reaction product. By using the characteristic, the information-acquiring device can acquire the fixed state of the objective substance to be detected on the surface of the sensing element, or equivalently, the presence or absence and the amount of the objective substance to be detected on the surface of the sensing element in more detail or more sensitively.

Figure 12:
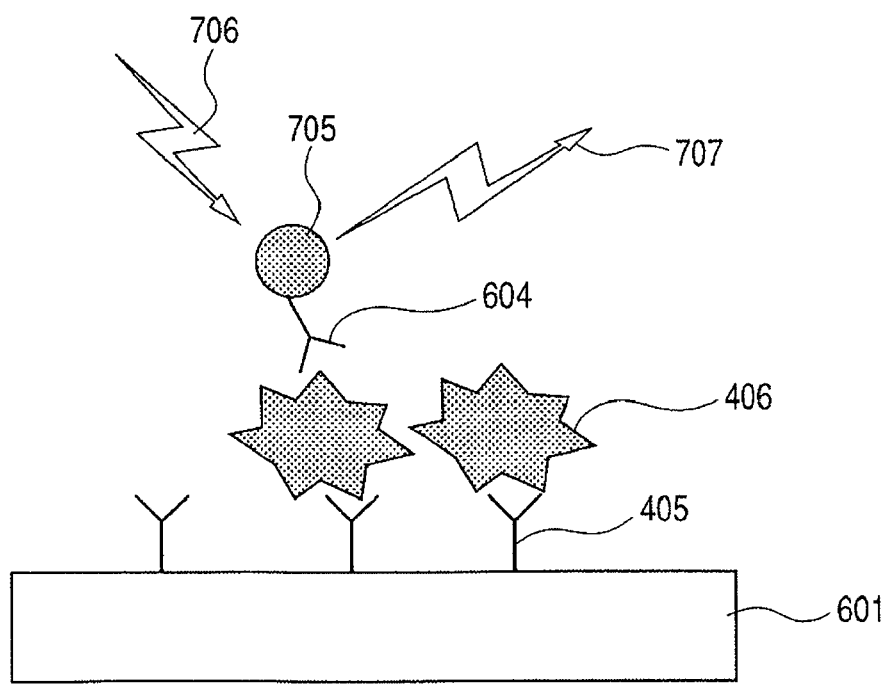
FIG. 12 is a view showing a sensing element using a fluorescent label.

FIG. 12 shows a detecting technique with the use of a fluorescence label. This technique employs a capturing body 604 indicated with a fluorescent dye 705, in the place of the capturing body 604 indicated with an enzyme 605 used in a detecting technique with the use of the enzyme label as is described in the example in FIG. 11. As the fluorescent dye, fluorosceinisothiocyanate, Cy3 and Cy5 are often used. The fluorescent dye 705 absorbs exciting light 706 and emits fluorescent light 707. The fluorescence 707 changes the spectrum intensity of the light which the sensing element receives, so that the sensing element can determine the fixed state of the objective substance to be detected on the surface of the sensing element, or equivalently, the presence or absence and the fixed amount of the objective substance to be detected on the surface. In the above detecting technique, a wavelength-limiting light filter for blocking the exciting light may be arranged at a suitable position, so that the exciting light 706 cannot affect a light-receiving element 103.

(Optical Configuration)

An optical configuration will be now described with reference to FIG. 1.

A substrate 101 may be a printed circuit board or a semiconductor substrate. A preferable substrate material includes Si (silicon) and GaAs (gallium arsenic).

A light Source 102 is installed on the substrate 101. The light source 102 is not particularly limited as long as it emits a sufficient quantity of light in an objective wavelength region, but a light-emitting element, particularly, a light emitting diode and a semiconductor laser are preferable. Further preferable is a LED made of a compound containing at least one of Ga (gallium), N (nitrogen), In (indium), Al (aluminum) and P (phosphorus).

Light 109 emitted from a light source 102 reaches light-receiving means 103 via wavelength-varying means. Usable wavelength-varying means is mainly conventional spectral means such as a diffraction grating. The examples of such spectral means include a transmission grating, a reflecting diffraction grating and a prism. FIG. 1 shows an example using the reflecting diffraction grating. Though depending on a diffraction efficiency, it is preferable to use a blaze type reflecting diffraction grating, and use the free spectral region of primary diffraction rays for detection. In addition, it is more preferable to place a filter for limiting wavelengths, which is not shown in FIG. 1, above the light source, so as to avoid stray light originating in light having wavelengths other than the free spectrum. The device shown in FIG. 1 further employs a concave mirror 108 as wavelength-varying means, which leads/focuses spectral light reflected by a diffraction grating 107 to/on a light-receiving element 103. The concave mirror narrows a detecting wavelength range for every light-receiving means, and improves the overall accuracy of spectrometry. The device shown in FIG. 1 also can employ a concave diffraction grating in place of the concave mirror 108 and a plane mirror in place of a planar plane diffraction grating 107, which configuration can be adopted as one aspect according to the present invention. The power of the concave diffraction grating 107 is preferably set so that the spectral light reflected by the concave diffraction grating can form an image on the light-receiving element 103.

Light-receiving means 103 has light-receiving elements. More specifically, the light-receiving element is preferably a photodiode made of Si when a receiving light has wavelengths in a visible light region, a photodiode made of GaAsP when having only to detect wavelengths only in a blue region out of a visible light region, and a photodiode made of InGaAs when having only to detect wavelengths only in an infrared region. In addition, the light-receiving means 103 has preferably a configuration in which light-receiving elements are arrayed. The preferable combination of the materials of a substrate 101, a light-emitting element 102 and the light-receiving means 103 should be selected in accordance with an operating wavelength region, but the substrate 101 is preferably a Si substrate from the viewpoint of a cost.

Figure 9:
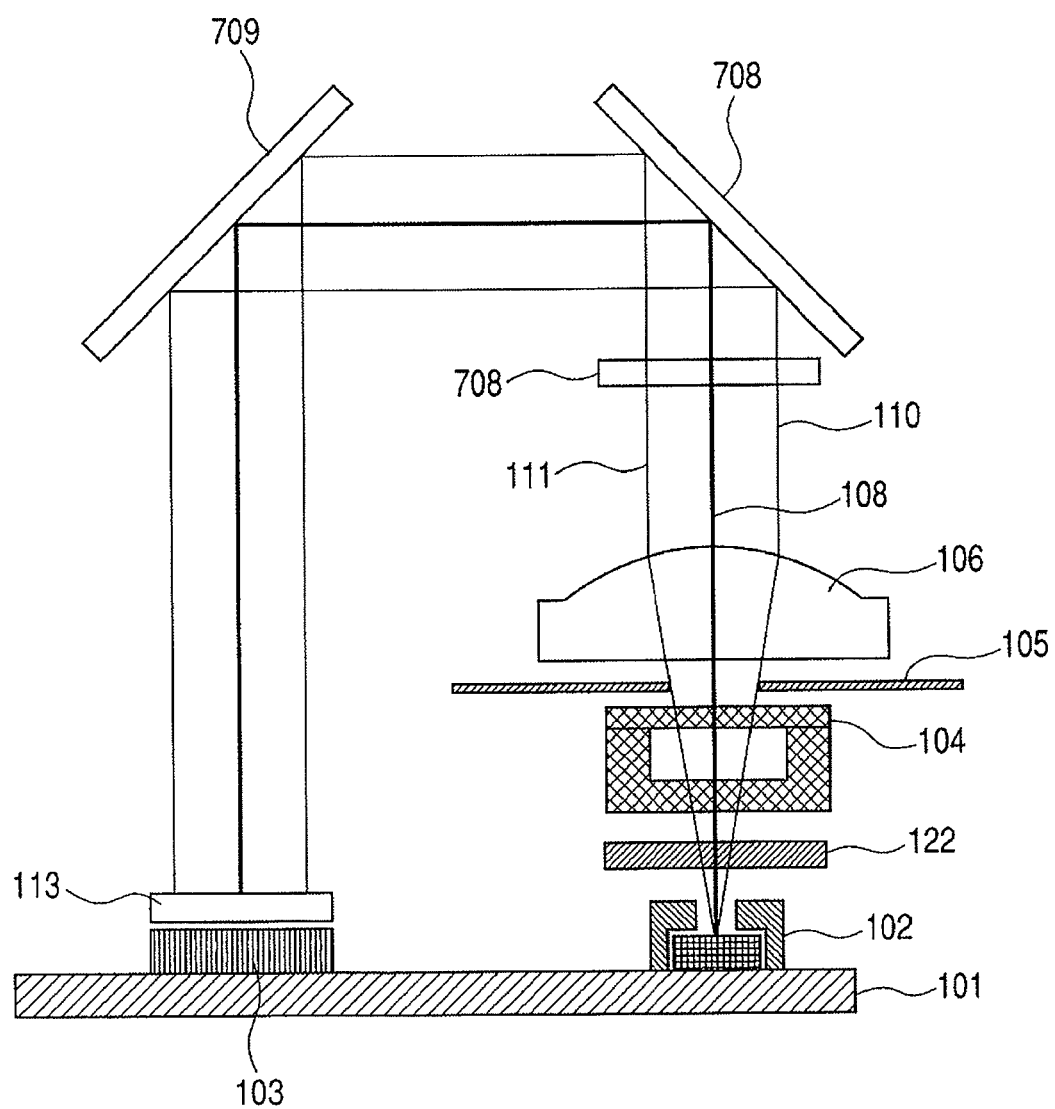
FIG. 9 is a schematic block diagram showing one example of an information-acquiring device.

When means for each varying the wavelength regions of light incident on each of a plurality of the light-receiving means is noted, an information-acquiring device according to the present invention can be divided into two aspects of (1) using spectral means (FIGS. 1, 2, 3, 9 and 5) and (2) using an optical filter (FIGS. 7 and 9), from the viewpoint of the above means.

Figure 3:
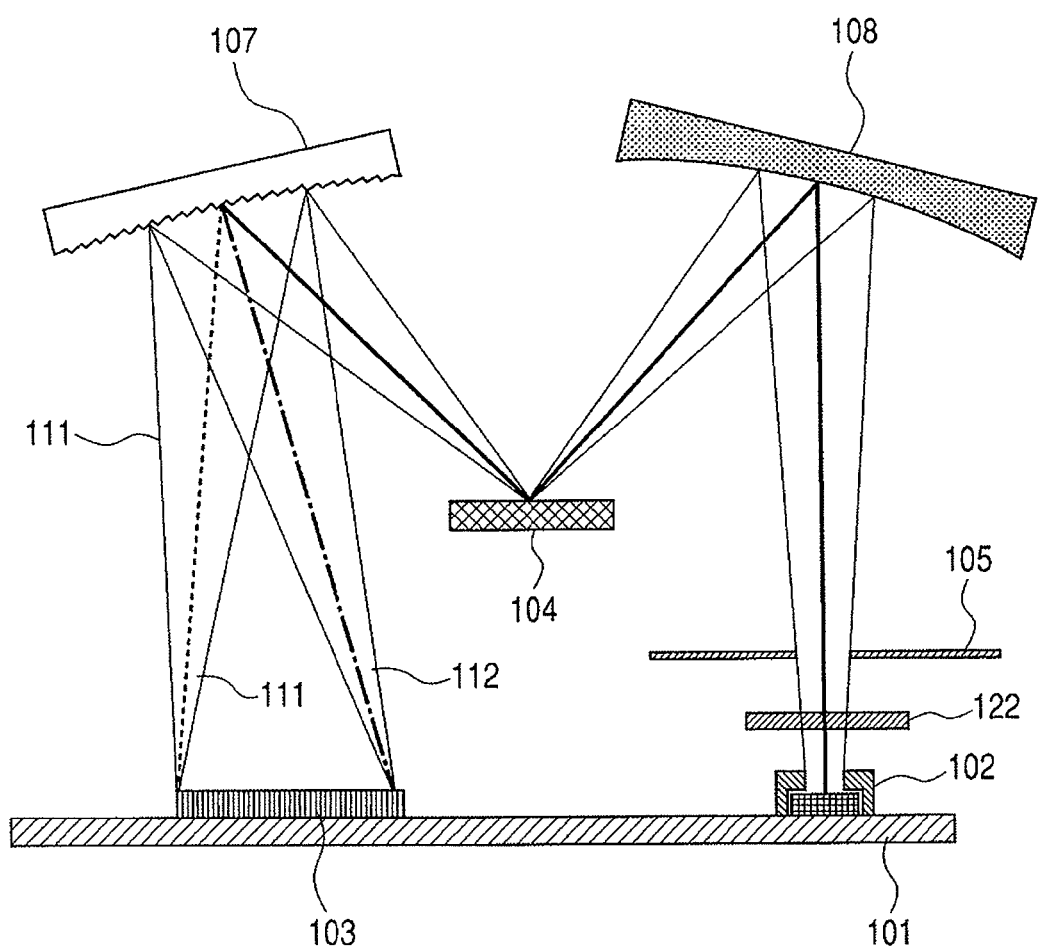
FIG. 3 is a schematic block diagram showing one example of an information-acquiring device.
Figure 4:
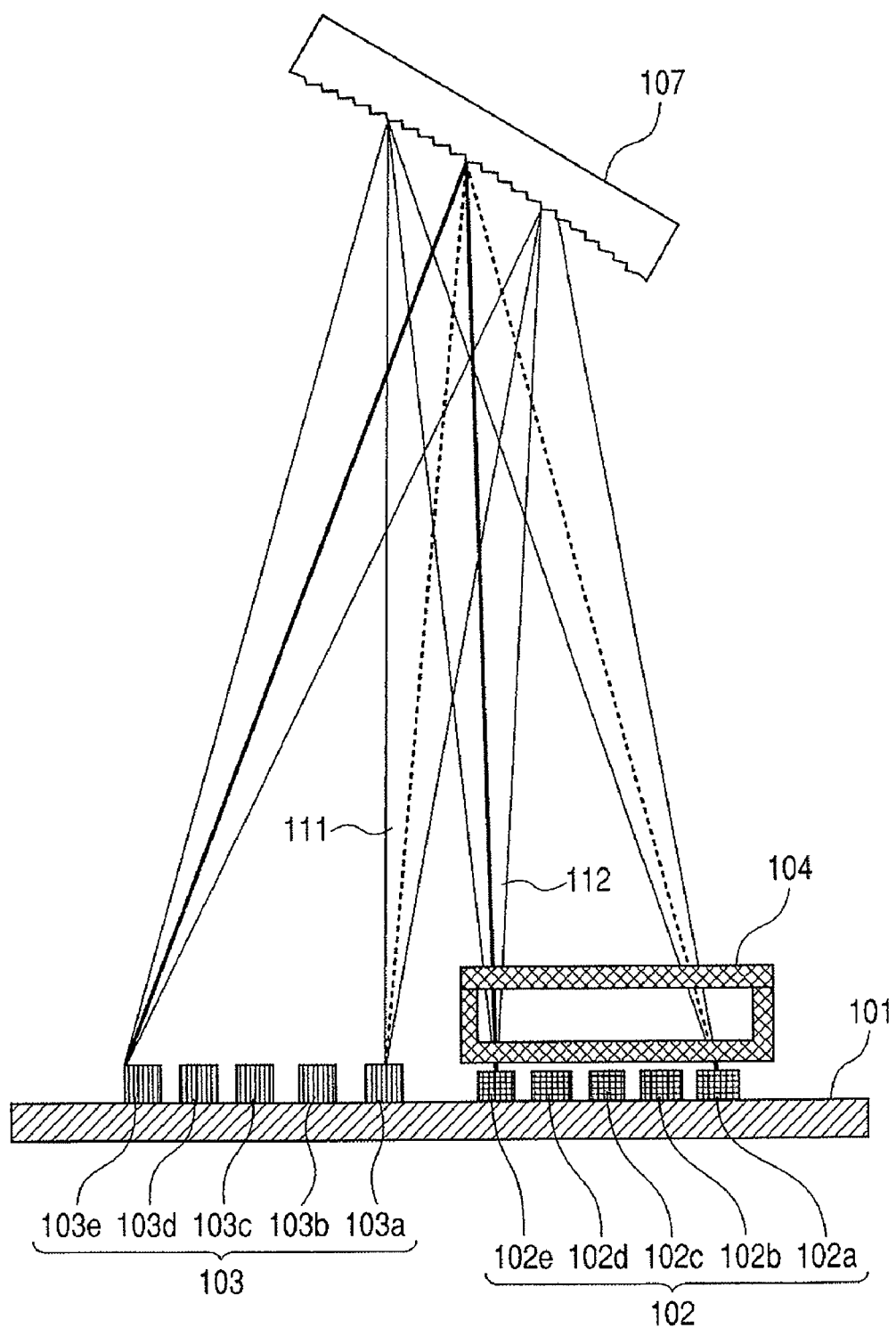
FIG. 4 is a schematic block diagram showing one example of an information-acquiring device.
Figure 5:
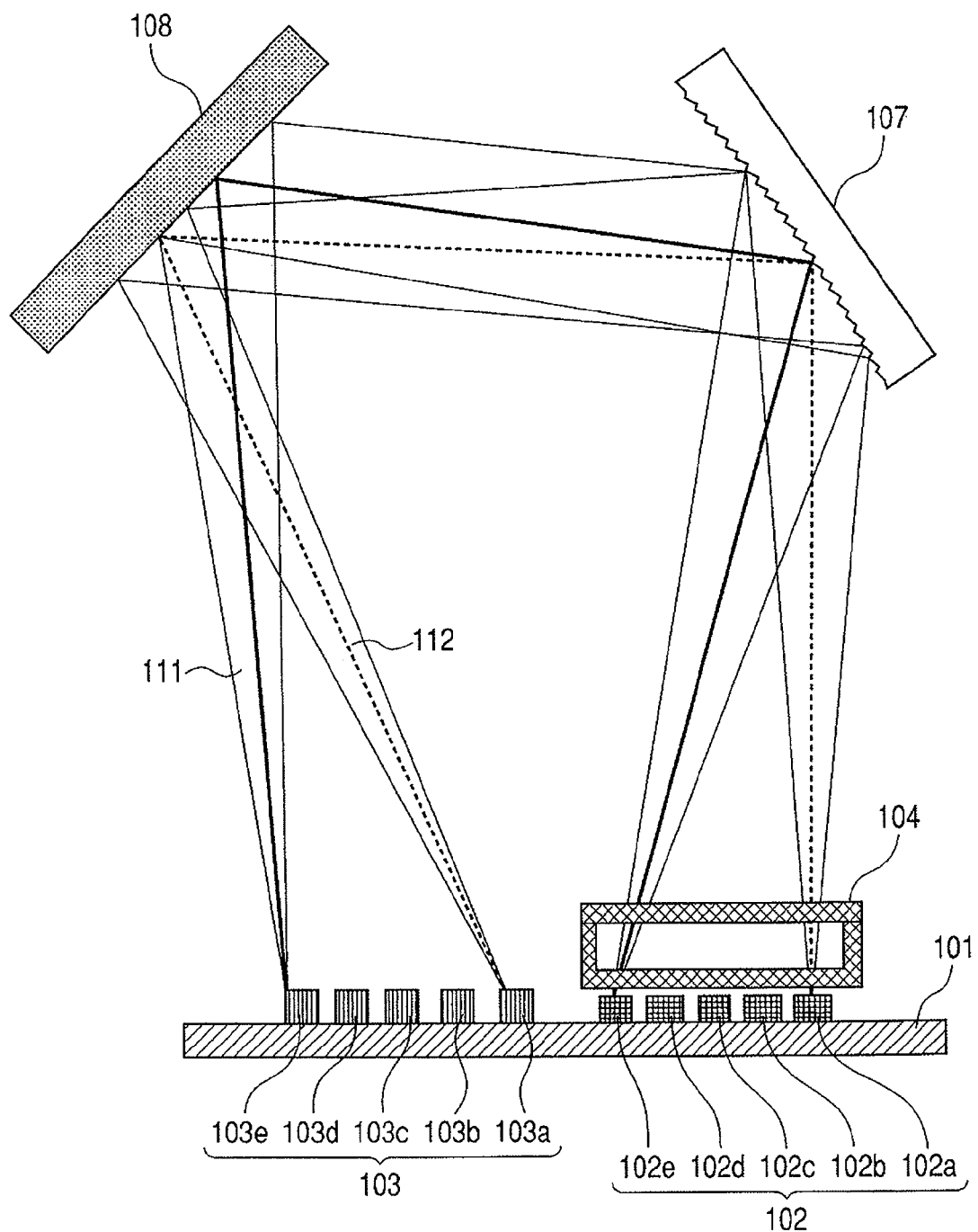
FIG. 5 is a schematic block diagram showing one example of an information-acquiring device.

(1) First of all, an aspect of using spectral means will be described. The aspect can be divided into two aspects of (i) an aspect having one light source (FIGS. 1, 2, 3, 7 and 9) and (ii) an aspect of switching a plurality of the light sources (FIGS. 4 and 5).

(i) Aspect Having One Light Source

In an aspect described here, light emitted from one light source is divided into several wavelength ranges by spectral means, and a plurality of light-receiving means receive each divided light having each different wavelength range.

Light emitted from a light source 102, as shown in FIGS. 1, 2, 7 and 9, is narrowed by a light shield 105, is converted to parallel rays by a collimating lens 106, and reaches light-receiving means 103 via the above described wavelength-varying means and sensing element 104 according to the present invention. The light-receiving means 103 is a sensor array in which light-receiving elements are linearly placed and configured.

The aspect is preferably configured to have a filter 122 for limiting wavelengths (hereafter called a "stray-light-avoiding filter") on a light-emitting element, in order to avoid the stray light due to the light having the wavelengths other than a free spectral region.

(ii) Aspect of Arranging a Plurality of Light Sources and Switching Them

In an aspect described here, an information-acquiring device has a plurality of light sources, can make selectively each light source emit light by using means for switching the light sources, divides each light into several wavelength ranges by spectral means, and make a plurality of light-receiving means receive the light having different wavelength ranges. The aspect will be now described with reference to FIGS. 4, 5 and 6.

In every aspect in each figure, a light-emitting element is used as a light source 102. A plurality of light-emitting elements are linearly placed on a substrate. A plurality of the light-emitting elements can sequentially emit light in a preset order through a function of switching means which has a control circuit installed on the substrate 101 or separately installed. Each light-emitting element may have its wavelengths or wavelength region optimally set so as to fit the wavelengths of the light which will be received by a corresponding light-receiving element, but a plurality of light-emitting elements may employ the same light-emitting element if it has wide wavelengths.

Light-receiving means 103 has a plurality of light-receiving elements arrayed. Light emitted from a light-emitting element is divided into several wavelength regions by a diffraction grating 107. For the diffraction grating, a blaze type reflection grating is preferably used.

Figure 6:
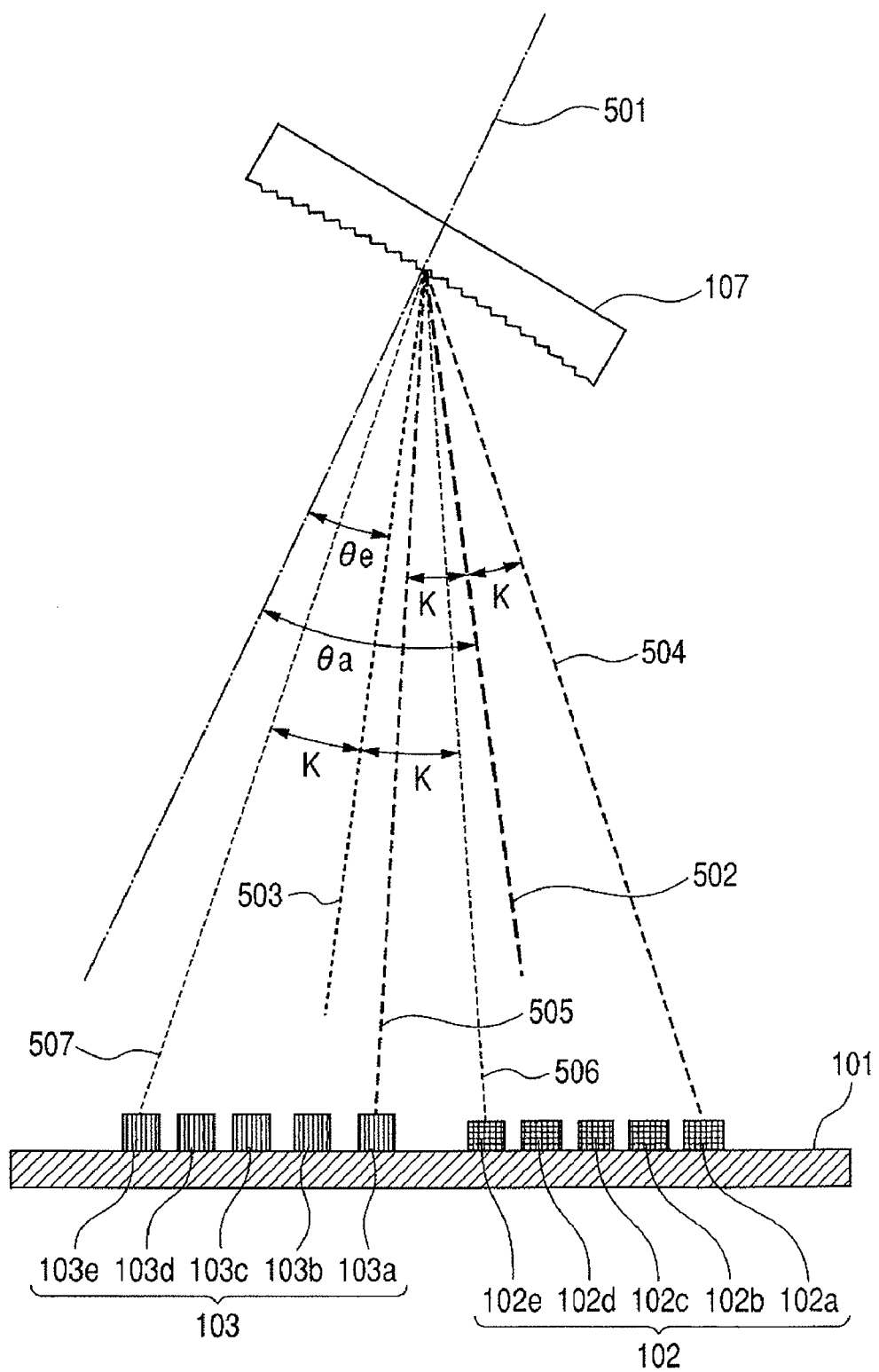
FIG. 6 is a schematic block diagram showing one example of an information-acquiring device.

The optimal arrangement of a light-emitting element 102, a light-receiving element 103 and a diffraction grating 107 will be now described with reference to FIG. 6. Each of light sources 102a to 102e respectively corresponds to each of light-receiving elements 103a to 103e one-on-one. A pair of corresponding elements is called an "element pair". A pair of the light-emitting element 102a and the light-receiving element 103a is called an "element pair (a)". Each of light-emitting elements 102a to 102e and each of light-receiving elements 103a to 103e are arranged so that an angle formed by a line which connects each former element with the center of a diffraction grating 107 and a line which connects each latter element with the center can have a constant deflection angle 2 K. For instance, the angle formed by the line 504 which connects the light-emitting element 102a and the center of the diffraction grating of 107 and the line 505 which connects the light-receiving element 103a and the center becomes 2 K. Thus formed angle by the lines which connect each of the element pair and the center of the diffraction grating is hereafter called an "angle by element pair". A dashed line 502 is a line which divides the angle into equal halves (hereafter called a "bisector line"). Accordingly, each angle formed by a line 502 and the lines 504 and 505 is K. The angle θ formed by each bisector line in the element pairs (a) to (e) and the normal line 501 of the diffraction grating is respectively determined to be θa to θe. When the light sources of emitting light are sequentially switched from the light-emitting elements 102a to 102e in the arrangement, the wavelength λ of the light which the corresponding light-receiving element receives becomes λ=(2 sin θ·cos K)/mN. In the above expression, N is the number of the teeth of the diffraction grating and is constant, and m is an order of diffraction, while light by ±1 order of diffraction is generally used. It is clear from the expression that when θ is sequentially switched from θa to θe by switching the light-emitting elements, the wavelength is also switched. The light-emitting elements having optimal characteristics for emitting the light with each wavelength are preferably arranged for the light sources 102(a) to 102(e) so as to correspond to each wavelength.

Figure 13:
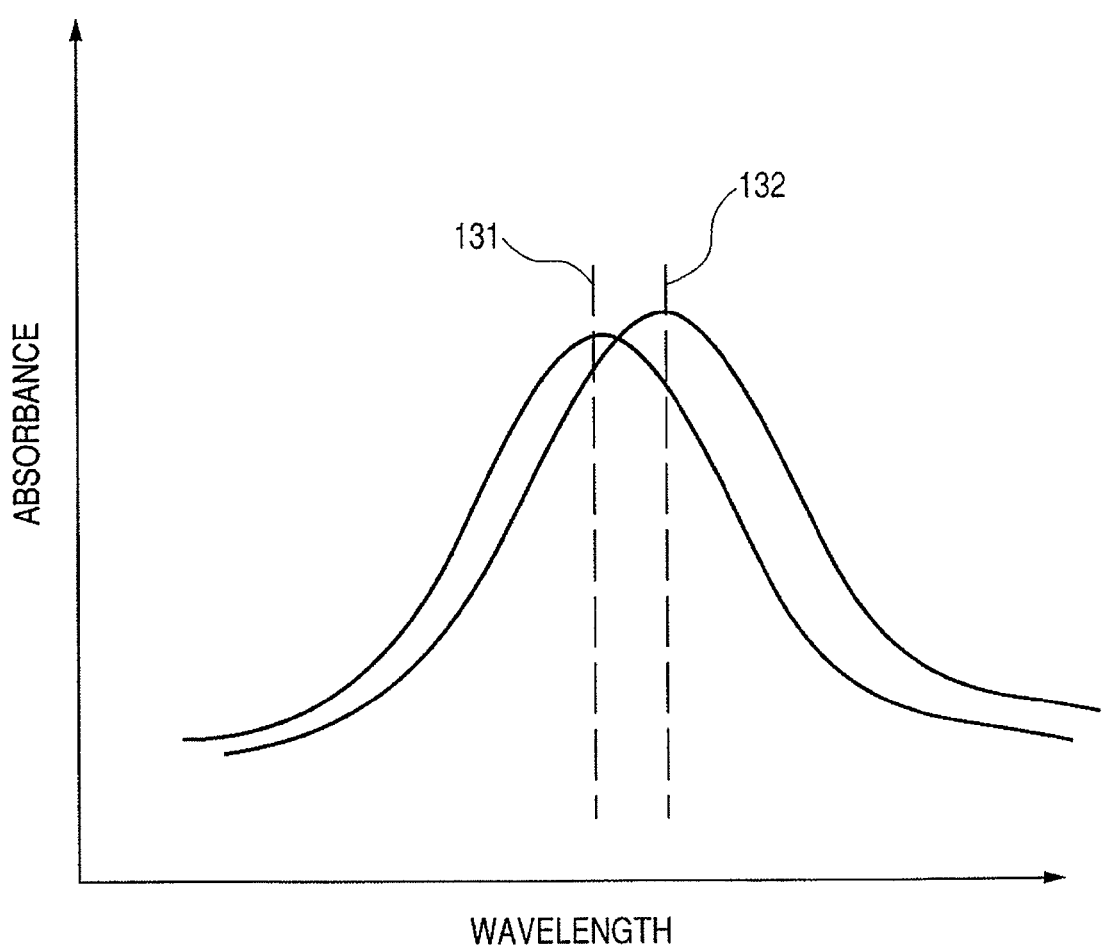
FIG. 13 is a view showing a spectral change caused by localized plasmon resonance.

A configuration in a specific system will be now described. The present aspect employs a detecting method using localized plasmon resonance caused by gold nanoparticles. An absorption spectrum by the localized plasmon of gold nanoparticles has a shape as shown in FIG. 13. When the gold nanoparticles have the diameter of 40 nm, the peak absorption wavelength in an aqueous solution is around 530 nm. In order to acquire the waveform of absorbed light, it is sufficient to acquire only a spectrum in a wavelength region between 450 nm and 600 nm. One example of the diffraction grating, the above described angle K and the range of above described angle θ was designed, and is described below.

When N is 600 Line/mm, K is 61.6 degree and m is −1, θ corresponding to 450 nm is −9.04 degree, and θ corresponding to 600 nm is −12.10 degree. An optical system can be composed by arranging the light-emitting element and the light-receiving element at each corresponding position. When a LED is used for the light-emitting element in the above arrangement, a single LED is difficult to cover 450 to 600 nm because a general LED has a half-width of a wavelength of about 50 nm, so that a plurality of LEDs are preferably employed in order to cover the wavelength range. For instance, by using a blue LED for a wavelength zone of 450 nm to 500 nm, using a green LED for 500 nm to 550 nm, and using a yellow LED for a wavelength zone of 550 nm to 600 nm, the device according to the aspect can cope with spectrometry requiring a wide wavelength range by using a light-emitting diode.

(2) Aspect of Using Optical Filter

A device according to the present aspect varies the wavelength or the wavelength region of light incident on each of a plurality of light-receiving elements, by using an optical filter. The aspect will be now described with reference to FIG. 7. In the present aspect as well, other components than being described here can employ the components previously described in other aspects.

Reference numerals 708 and 709 are reflecting mirrors of reflecting means for changing a traveling direction of light emitted from a light-emitting element.

Reference numeral 113 is an optical filter for limiting the wavelength of light input to a light-receiving element array, divides light into several wavelength regions light, and inputs a particular wavelength or a wavelength region into each light-receiving element. The optical filter is not particularly limited as long as it provides a desired zone, but an interference filter using a dielectric multilayer film is preferable. The optical filter 113 varies wavelengths of lights which a plurality of optical elements receive, and enables a sensing element to determine optical transmittance in each wavelength or wavelength region. Specifically, the optical filter makes each light-receiving element receive each of a plurality of the wavelengths or the wavelength regions provided by dividing the predetermined wavelength region necessary for forming a wavelength-absorption spectrum. Thereby, the device can obtain an absorption spectrum over the predetermined wavelength region.

EMBODIMENTS

The present invention will be now described below with reference to embodiments, but the present invention is not limited to these embodiments. In addition, repeated description on common matters to each embodiment is omitted.

Embodiment 1

Embodiment 1 will be now described with reference to FIG. 1. A white light-emitting diode 102 and a photodiode array 103 are placed on a printed circuit board 101.

A sensing element 104 which is made of a flow cell made of an optically transparent glass, uses localized plasmon resonance, and has a structure shown in FIG. 10, is manufactured by the following steps of: treating a detecting region of an inner face of a channel of the flow cell with an aminosilane coupling agent to form the inner face having an amino group exposed thereon, filling it with an aqueous solution containing gold nanoparticles with diameters of 20 to 40 nm (made by Tanaka Kikinzoku Kogyo K. K. Corporation) to fix gold nanoparticles thereon; subsequently, immobilizing an antibody on the gold nanoparticles as a capturing body; specifically, surface-modifying the gold nanoparticles with an ethanol solution of 11-Mercaptoundecanoicacid having a thiol group having a high affinity for gold, by contacting the solution with the detecting region of the flow cell having the gold nanoparticles fixed thereon, to thereby expose a carboxyl group on the surfaces of the gold nanoparticles; in the state, adding an aqueous solution of N-Hydroxysulfosuccinimide (made by Dojindo Laboratories Corporation) and an aqueous solution of 1-Ethyl-3-[3-dimethylamino]propyl]carbodiimide hydrochloride (made in Dojindo Laboratories Corporation) dropwise into the detecting region, to thereby expose a succinimide group on the surfaces of the gold nanoparticles; subsequently, putting a solution of rabbit antimouse IgG antibody buffered by phosphoric acid (pH 8.0), which is an antibody to be immobilized and has specificity for a substance to be detected, in the flow cell; and immobilizing the rabbit antimouse IgG antibody on the gold surface, by reacting the above described succinimide group arranged on the gold surface with the amino group of the rabbit antimouse IgG antibody. With the above method, the sensing element was prepared.

A sensing element 104 was arranged in an optical path from a light emitting diode 102 to a diffraction grating 107.

Figure 14:
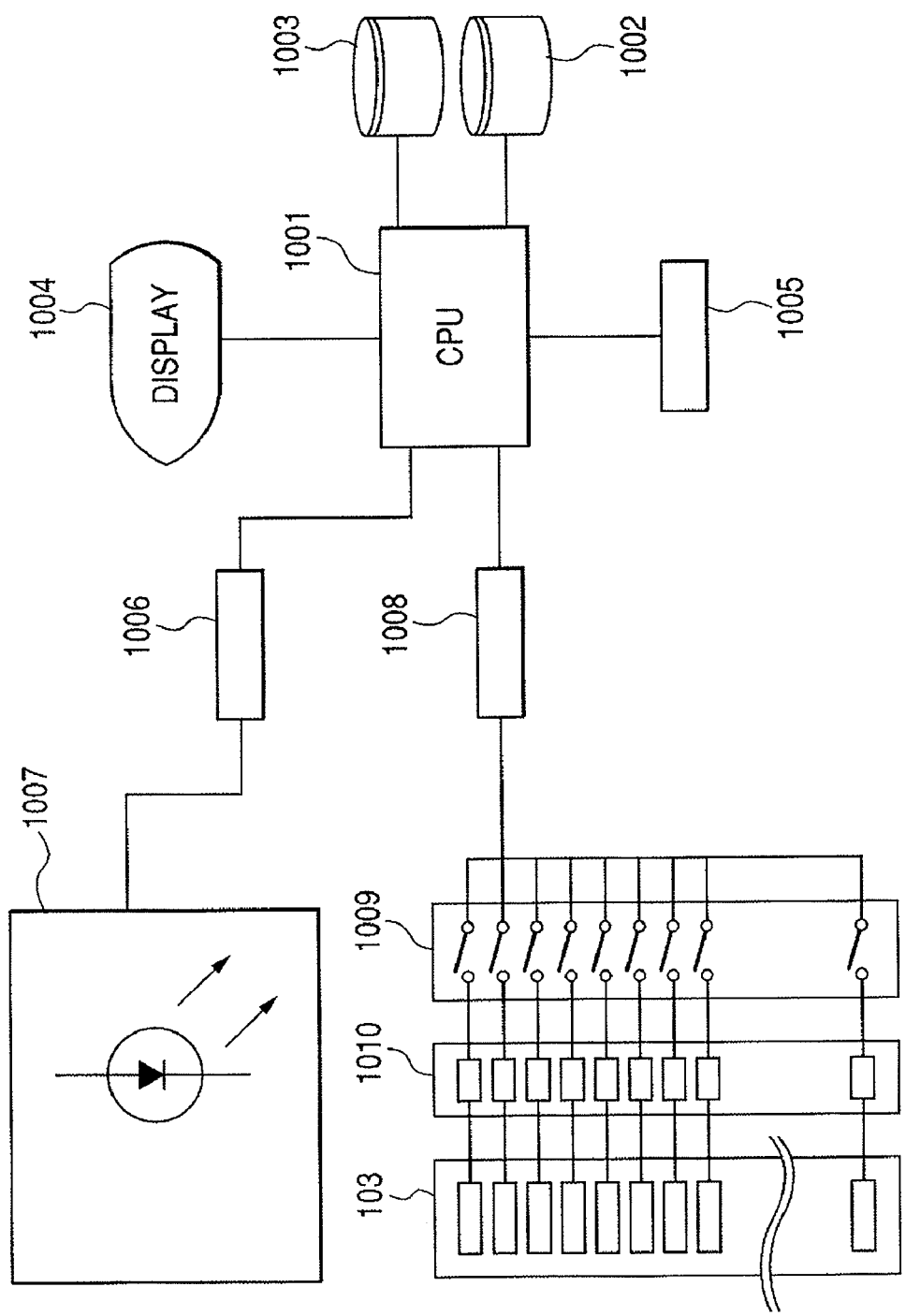
FIG. 14 is a block diagram showing one example of a configuration of a device according to the present invention.

A collimating lens 106 converts the light into parallel rays, which has been emitted from a light-emitting diode 102, has been transmitted through a stray-light-avoiding filter 122 and a sensing element 104, and has passed through a light shield 105. The parallel rays are incident on a diffraction grating 107. The diffraction grating 107 diffracts a ray of light with the longest wavelength to the ray of the light shown by 111, and diffracts the ray of light with the shortest wavelength to the ray of the light shown by 112. A concave mirror of 108 focuses thus divided light onto a photodiode array 103, and narrows a wavelength range to be detected by every photodiode of a light-receiving element to improve the overall accuracy of spectrometry. Thereby, the light with various wavelength ranges is incident on each photodiode of the photodiode array 103. By detecting output signals from all elements of the photodiode array 103, the device acquires an absorption spectrum of localized plasmon resonance in a sensing element 104. A method for treating the signals output from the photodiode will be now described with reference to FIG. 14. It is presumed that each output from the photodiodes 103 has been already converted to voltage by a current-voltage converter circuit. In the figure, the current-voltage converter circuit is not shown, but generally a circuit using an operational amplifier is used for it. A hold circuit 1010 holds the output from each photodiode. The hold circuit plays a role of simultaneously sampling each photodiode and holding the obtained output. A multiplexer 1009 inputs the output held by the hold circuit into an AD converter 1008. Here, the multiplexer is used, but a shift register may be used. The AD converter converts input data into digital data, and a CPU 1001 processes the converted values and converts them into spectral data. The above described signal processing method is common in each embodiment.

Because of detecting light by using localized plasmon resonance in each embodiment, the device can acquire spectral data described in FIG. 13. A processing method will be described below.

Now, a change in a sensing element 104 will be described with reference to FIGS. 10A to 10D. A metallic nanoparticle 402 has capturing bodies 405 immobilized on its surface. In the present embodiment, an antibody specifically coupled with an objective substance to be detected is used for the capturing body. When the antibody captures the objective substance 406 to be detected, a refractive index around the metal nanoparticle 402 is changed. Thereby, as is shown in FIG. 13, a peak absorption wavelength by localized plasmon resonance around the metal nanoparticle 402 is shifted from 131 measured before capturing to 132 measured after capturing. The amount of the objective substance to be detected in an unknown specimen can be determined, on the basis of a working curve which has been determined from the variation of the absorption peak and the known amount of the objective substance to be detected.

Embodiment 2

Embodiment 2 will be now described with reference to FIG. 2.

A sensing element 104 according to the present embodiment uses localized plasmon resonance shown in FIG. 10, as in the case of the first embodiment, but in the present embodiment, the sensing element 104 is placed in an optical path from a concave mirror 108 to a photodiode array 103 as shown in FIG. 2. Reference numeral 114 shows a sensing portion in the sensing element 104. The device can acquire an absorption spectrum of localized plasmon, by making the photodiode array 103 detect spectral light after having passed through the sensing portion 114. When the sensing portion is smaller than the photodiode array 103 as shown in FIG. 2, it cannot acquire the all spectrum of the whole sensing portion. Accordingly, the device can acquire the spectrum in the whole objective wavelength range at the sensing portion 114, by acquiring the signals of the photodiode while moving the sensing element 104 in the direction of the photodiode 103.

Embodiment 3

Embodiment 3 will be now described with reference to FIG. 3. A device according to the present embodiment has a concave diffraction grating 107 arranged in a position of a concave mirror 108 in FIG. 1; the concave mirror 108 arranged in a position of a plane diffraction grating 107 in FIG. 1; and sensing means 104 arranged between them.

A concave mirror 108 is arranged so as to reflect light which has passed through a light shield 105, and focus the light on a sensing element 104. The sensing element 104 reflects the light so as to be incident on a concave diffraction grating 107. The concave diffraction grating 107 diffracts a ray of light with the longest wavelength to the ray of the light shown by 111, and the ray of the light with the shortest wavelength to the ray of the light shown by 112. The concave power of the diffraction grating 107 makes spectral light diffracted here focus on a photodiode array 103, and specifically makes the light with each different wavelength range incident on each photodiode of the photodiode array 103. As described above, the concave diffraction grating 107 narrows the wavelength range to be detected by every light-receiving element, and improves the overall accuracy of spectrometry.

A sensing element 104 is am element with a sensing label using an enzyme as shown in FIG. 11. Alternatively, the sensing element using fluorescence as shown in FIG. 12 may be used. The sensing element employs horseradish peroxidase as an enzyme 605, and 1,2-phenylenediamine as an enzyme substrate 606. Consequently, an enzyme product 607 is produced which has absorption in 491 nm. The amount of an objective substance to be detected can be determined by measuring the absorption in 491 nm.

Embodiment 4

Embodiment 4 will be now described with reference to FIG. 4. This device has white light emitting diodes 102a to 102e and photodiode arrays 103a to 103e arranged on a printed circuit board 101. Here, five light-emitting elements 102 and five light-receiving elements 103 are shown in a diagram, for reasons of description, but are not always limited to the configuration. The positions of the elements are set so that the angles formed by element pairs (a) to (e) with respect to a diffraction grating have the same constant deflection angle. The device employs the same sensing element 104 using localized plasmon resonance, which has been prepared with the same method as in Embodiment 1. Light emitted from each light-emitting element passes through the sensing element and is incident on a concave diffraction grating 107. The used diffraction grating 107 is a concave grating for an aberration correction type constant deflection angle monochrometer made by Shimadzu Corporation, which is a blaze type diffraction grating and is suitable for the present embodiment. The concave diffraction grating diffracts a ray of light with the longest wavelength to the ray of the light shown by 111, and diffracts the ray of light with the shortest wavelength to the ray of the light shown by 112. Then, the device sequentially switches the light-emitting elements 102a to 102e from which the light with the fixed wavelength corresponding to each light-emitting element can be taken out, and simultaneously detects the signals output from the light-receiving elements 103e to 103a to acquire the absorption spectrum due to the localized plasmon resonance which occurs in the sensing element 104.

In the above, an embodiment was described while referring to a configuration in FIG. 4, but an optical system with the use of a reflecting mirror 108 in an optical path may be configured as shown in FIG. 5.

Embodiment 5

Figure 7:
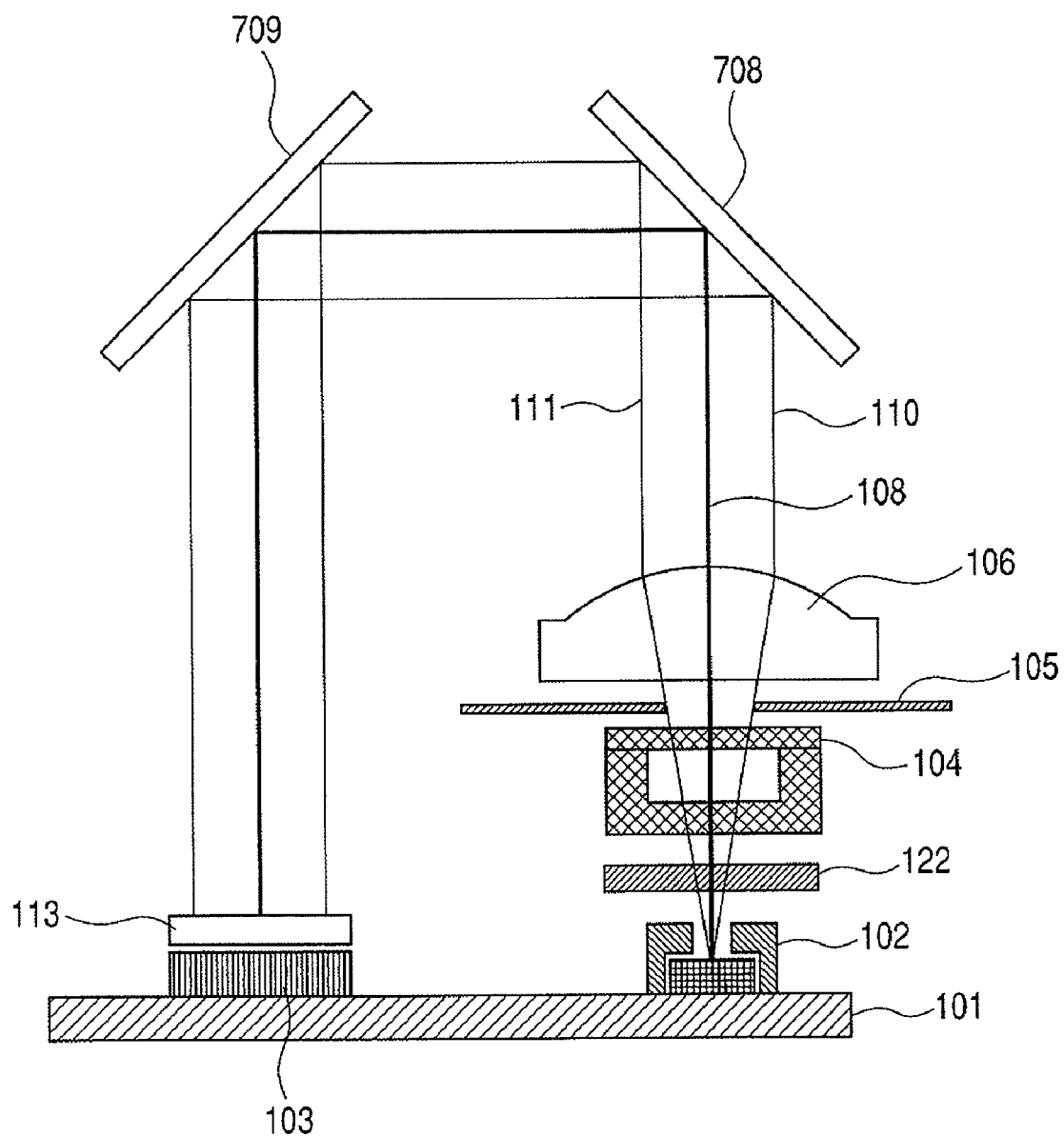
FIG. 7 is a schematic block diagram showing one example of an information-acquiring device.
Figure 8:
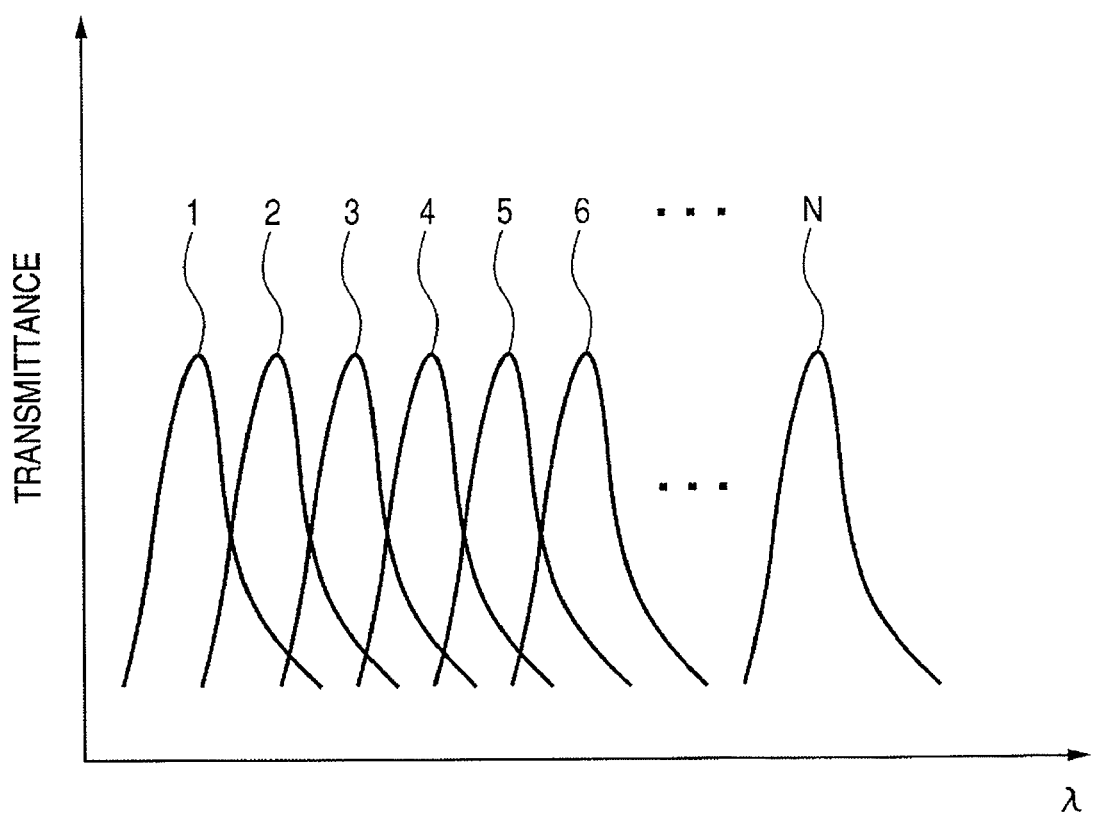
FIG. 8 is a schematic block diagram showing wavelength characteristics of a transmitted light through a filter.

Embodiment 5 will be now described with reference to FIG. 7. This device employs the same sensing element 104 using localized plasmon resonance, which has been prepared with the same method as in Embodiment 1. The device makes light sequentially transmitted through the sensing element 104 and a light shield 105, and converted into parallel rays by a collimating lens 106, and makes the parallel rays sequentially incident on reflecting mirrors 708 and 709 to change the traveling direction of the rays, and the changed rays incident on an interference filter 113. The interference filter 113 leads incident lights having each desired wavelength to each element of a photodiode array 103, so that the sensing element 104 can detect them. FIG. 8 shows the spectral characteristics of the interference filter 113. Each filter having the characteristics corresponding to the number 1 to N is placed at the front of each corresponding photodiode. Thereby, the light having each different wavelength range is incident on each photodiode of the photodiode array 103. Accordingly, the device can acquire an absorption spectrum of localized plasmon resonance which occurs in the sensing element 104, through detecting signals of all picture elements output from the photodiode array 103.

This application claims priority from Japanese Patent Application Nos. 2004-270501 filed Sep. 16, 2004, 2004-270572 filed Sep. 16, 2004 and 2004-270574 filed Sep. 16, 2004, which are hereby incorporated by reference herein.

The invention claimed is:

1. A sensing device for detecting an objective substance in a specimen by utilizing localized plasmon resonance, comprising:
   a light source;
   a light receiving unit;
   a supporting unit for supporting a member having a nano-metal structure to give rise to the localized plasmon resonance by receiving light emitted from the light source; and
   a substrate supporting the light source and the light receiving unit,
   wherein a spectral unit is provided in an optical path between the light source and the light receiving unit, and
   wherein the supporting unit is located such that light emitted from the light source is transmitted through the member towards the light receiving unit.

2. A sensing device according to claim 1, wherein the spectral unit comprises a diffraction grating.

3. A sensing device according to claim 1, wherein the spectral unit comprises a prism.

4. A sensing device according to claim 1, wherein a reflecting unit for leading light from the light source to the light receiving unit is provided in the optical path.

5. A sensing device according to claim 4, wherein the reflecting unit comprises a mirror.

6. A sensing device according to claim 5, wherein the mirror is a concave mirror.

7. A sensing device according to claim 1, wherein the objective substance is detected based on a shift of an absorbed peak wavelength of the light.

* * * * *